United States Patent
Sharma et al.

(10) Patent No.: US 10,690,532 B2
(45) Date of Patent: Jun. 23, 2020

(54) MULTI-PHASE FLUID FRACTION MEASUREMENT

(71) Applicant: GENERAL ELECTRIC COMPANY, Schenectady, NY (US)

(72) Inventors: Prafull Sharma, Karnataka (IN); Aparna Chakrapani Sheila-Vadde, Karnataka (IN); Suma Memana Narayana Bhat, Karnataka (IN); Vikram Melapudi, Karnataka (IN)

(73) Assignee: Baker Hughes Oilfield Operations LLC, Houston, TX (US)

( * ) Notice: Subject to any disclaimer, the term of this patent is extended or adjusted under 35 U.S.C. 154(b) by 18 days.

(21) Appl. No.: 15/525,905

(22) PCT Filed: Oct. 14, 2015

(86) PCT No.: PCT/US2015/055424
§ 371 (c)(1),
(2) Date: May 10, 2017

(87) PCT Pub. No.: WO2016/077011
PCT Pub. Date: May 19, 2016

(65) Prior Publication Data
US 2017/0322064 A1    Nov. 9, 2017

(30) Foreign Application Priority Data
Nov. 10, 2014    (IN) .......................... 5645/CHE/2014

(51) Int. Cl.
*G01F 1/74*    (2006.01)
*G01F 1/66*    (2006.01)
(Continued)

(52) U.S. Cl.
CPC .................. *G01F 1/74* (2013.01); *G01F 1/66* (2013.01); *G01N 22/00* (2013.01); *G01N 33/2823* (2013.01)

(58) Field of Classification Search
CPC .. G01F 1/66; G01F 1/74; G01N 22/00; G01N 33/2823
(Continued)

(56) References Cited

U.S. PATENT DOCUMENTS

| 5,243,290 A | 9/1993 | Safinya et al. |
| 5,259,239 A | 11/1993 | Gaisford |

(Continued)

FOREIGN PATENT DOCUMENTS

| EP | 2 366 980 A2 | 9/2011 |
| WO | 2006/134456 A1 | 12/2006 |
| WO | 2013/181173 A | 12/2013 |

OTHER PUBLICATIONS

Meribout et al., "A Multisensor Intelligent Device for Real-Time Multiphase Flow Metering in Oil Fields," IEEE Transactions on Instrumentation and Measurement, vol. 59, Issue 6, pp. 1507-1519, (Jun. 2010).

(Continued)

*Primary Examiner* — Benjamin R Schmitt
(74) *Attorney, Agent, or Firm* — Mintz Levin Cohn Ferris Glovsky and Popeo, P.C.

(57) ABSTRACT

A method of determining a fraction of one or more phases in a multi-phase fluid in a conduit is provided. The method includes exciting (602) a sensing device to cause emission of electromagnetic waves of a range of frequencies into a multi-phase fluid. The sensing device comprises an antenna and a dielectric layer, selected to cause resonance in at least one of a first set of frequencies or a second set of frequencies based on a flow state of the multi-phase fluid, when placed (Continued)

proximate to the multi-phase fluid. The method also includes receiving (604) transmitted or reflected electromagnetic waves from the multi-phase fluid. The flow state of the multi-phase fluid is selected (606) based on a classification parameter. Fractions are determined (608) utilizing at least one fraction determination model that is selected based on the flow state of the multi-phase fluid.

20 Claims, 6 Drawing Sheets

(51) Int. Cl.
*G01N 33/28* (2006.01)
*G01N 22/00* (2006.01)

(58) Field of Classification Search
USPC .............................................. 73/202, 861.04
See application file for complete search history.

(56) References Cited

U.S. PATENT DOCUMENTS

| | | | |
|---|---|---|---|
| 5,485,743 | A | 1/1996 | Taherian et al. |
| 5,576,974 | A | 11/1996 | Marrelli et al. |
| 5,625,293 | A | 4/1997 | Marrelli et al. |
| 6,182,504 | B1 | 2/2001 | Gaisford |
| 6,466,035 | B1 | 10/2002 | Nyfors et al. |
| 6,826,964 | B2 | 12/2004 | Nyfors |
| 6,915,707 | B2 | 7/2005 | Nyfors et al. |
| 7,293,471 | B2 | 11/2007 | Lund Bø et al. |
| 7,481,118 | B2 | 1/2009 | Nyfors |
| 7,624,652 | B2 | 12/2009 | Wee et al. |
| 7,631,543 | B2 | 12/2009 | Wee |
| 7,649,188 | B2 | 1/2010 | Endo et al. |
| 7,770,469 | B2 | 8/2010 | Nyfors et al. |
| 8,027,794 | B2 | 9/2011 | Xie |
| 8,606,531 | B2 | 12/2013 | Pinguet et al. |
| 2007/0124091 | A1* | 5/2007 | Wee ........................ G01F 1/58 702/49 |
| 2008/0303534 | A1 | 12/2008 | Wee |
| 2010/0145636 | A1 | 6/2010 | Nyfors |
| 2011/0196625 | A1 | 8/2011 | Sheila-Vadde et al. |
| 2011/0290035 | A1 | 12/2011 | Wee et al. |
| 2011/0301877 | A1 | 12/2011 | Wee et al. |
| 2012/0111124 | A1 | 5/2012 | Hu |
| 2013/0009048 | A1 | 1/2013 | Xie et al. |
| 2014/0260659 | A1 | 9/2014 | Sheila-Vadde et al. |

OTHER PUBLICATIONS

Sharma, P. et al., Sensor Apparatus for Measurement of Material Properties, GE Application No. 2174/CHE/2012, filed on May 30, 2012.

Wylie et al., "RF sensor for multiphase flow measurement through an oil pipeline," Measurement Science and Technology, vol. 17, Issue 8, pp. 2141-2149, (Aug. 2006).

International Search Report and Written Opinion issued in connection with corresponding PCT Application No. PCT/US15/55424 dated Jan. 18, 2016.

International Preliminary Report on Patentability issued in connection with corresponding PCT Application No. PCT/US15/55424 dated May 16, 2017.

* cited by examiner

MULTI-PHASE FLUID FRACTION MEASUREMENT

BACKGROUND

Embodiments of the present invention relate generally to multi-phase flow metering, and more specifically, to the use of antennas in measuring multi-phase fluid fractions.

A multi-phase fluid refers to a composition that includes at least two phases of material. For example, multi-phase fluids may include some combination of oil, water, and gas. In process industries, oil and gas industries and other such areas, it is often necessary to accurately measure fractions and flow rate of phases of the multi-phase fluid flowing inside a pipeline. With smaller and deeper oil/gas wells with higher water content becoming more common around the globe, there is an enhanced need for multi-phase flow measurement techniques.

Commercially available sensors for measuring fractions in fluids in the petroleum industry are based on a variety of principles (either a single technique or a combination of several techniques). For example, impedance sensors, capacitive and/or inductive sensors, dual-energy gamma sensors, venturi meters, and microwave sensors (attenuation/phase/resonance) have all been used. Currently, there are numerous microwave-based flow metering sensors available offering varying degrees of sensitivity, complexity and costs.

In current microwave based sensing systems, one or more sensors are excited over a range of frequencies to emit electromagnetic waves and the power of reflected and/or transmitted electromagnetic waves is measured over that frequency range. The resonant frequency of the system depends on the permittivity (dielectric constant) of the medium inside the pipe. A resonant mode can be characterized by the resonant frequency, Q factor and the amplitude of the peak in the transmitted or reflected electromagnetic waves. The shift in resonant frequency, or Q factor, or amplitude of the transmitted or reflected electromagnetic waves corresponding to a change in composition is used to estimate the phase fraction of the fluid. The resonant frequency and Q factor hold a proportional relationship with the dielectric constant. For instance, as the water content increases in the multi-phase fluid, the effective dielectric constant increases and a change in the resonant frequency, caused by the dielectric constant of the water, decreases. Similarly, if the water is lossy, e.g., due to salinity, that will result in a decrease in Q-factor of the reflected electromagnetic waves. Estimation of phase fractions using the resonant frequency method becomes difficult as the water content increases since identification of the peaks in the transmitted or reflected electromagnetic waves becomes a challenge.

Furthermore, some of the microwave-based metering sensors are intrusive to the flow inside the pipe. Consequently, these sensors may be exposed to the flow of the material inside the pipe, thereby increasing the possibility of damage to the sensors and necessitating frequent replacement. In other scenarios, the flow of the material may be measured by diverting the actual flow of material inside the pipe through an external flow circuit. In certain other scenarios, a flow separator or a flow mixer may be used.

Accordingly, there is an ongoing need to improve the performance of multi-phase flow metering in lossy media.

BRIEF DESCRIPTION

According to one embodiment, a method of determining a fraction of one or more phases in a multi-phase fluid in a conduit is provided. The method includes exciting a sensing device to cause the sensing device to emit electromagnetic waves of a range of frequencies comprising a first set of frequencies and a second set of frequencies into a multi-phase fluid. The sensing device comprises an antenna and a dielectric layer that is placed proximate to the multi-phase fluid. The antenna and dielectric layer are selected such that based on a flow state of the multi-phase fluid resonance is observed in at least one of the first set of frequencies and the second set of frequencies. Further, the method includes receiving transmitted or reflected electromagnetic waves from the multi-phase fluid. Furthermore, the method includes selecting the flow state of the multi-phase fluid based on a classification parameter. The classification parameter is determined based on an analysis of the transmitted or reflected electromagnetic waves. The method also includes determining the fraction of the one or more phases in the multi-phase fluid utilizing at least one fraction determination model. The fraction determination model is selected based on the flow state of the multi-phase fluid.

According to another embodiment, a system for determining a fraction of one or more phases of a multi-phase fluid flowing in a conduit is provided. The system includes one or more sensing devices placed on or about the conduit. Each sensing device includes an antenna configured to emit electromagnetic waves over a range of frequencies. The at least one antenna is selected such that resonance is exhibited in a first set of frequencies based on a flow-state of the multi-phase fluid. Further, each sensing device also includes a dielectric layer placed proximate to the antenna such that one side of the dielectric layer is in direct contact with the multi-phase fluid. The antenna and dielectric layer are selected such that resonance is exhibited in at least one of the first set of frequencies and a second set of frequencies based on a flow-state of the multi-phase fluid. Furthermore, the system also includes a controller configured to excite the antenna in at least the first set and the second set of frequencies from the range of frequencies. The controller is also configured to acquire transmitted or reflected electromagnetic waves from the multi-phase fluid. Furthermore, the controller is configured to select the flow state of the multi-phase fluid based on a classification parameter. The classification parameter is determined based on an analysis of the transmitted or reflected electromagnetic waves in at least one of the first set of frequencies and the second set of frequencies. The controller is also configured to estimate the fractions of the one or more phases of the multi-phase fluid using a fraction determination model and one or more parameters determined from the transmitted or reflected electromagnetic waves. The fraction determination model is selected based on the selected flow state of the multi-phase fluid.

According to yet another embodiment, a method for determining a fraction of one or more phases in a multi-phase fluid comprising substantial portions of a lossy phase is provided. The method includes exciting a sensing device causing the sensing device to emit electromagnetic waves of a range of frequencies into the multi-phase fluid. The sensing device comprises an antenna and a dielectric layer that are selected such that resonance is exhibited at different frequencies from the range of frequencies based on a fraction of the lossy phase in the multi-phase fluid. Further, the method includes receiving transmitted or reflected electromagnetic waves from the multi-phase fluid. Furthermore, the method includes determining the fraction of the lossy phase in the multi-phase fluid utilizing at least one fraction determination model. The fraction determination model includes a relationship between one or more parameters determined from the transmitted or reflected electromagnetic waves and phase fractions.

DRAWINGS

Other features and advantages of the present disclosure will be apparent from the following more detailed description of the preferred embodiment, taken in conjunction with the accompanying drawings which illustrate, by way of example, the principles of certain aspects of the disclosure.

DETAILED DESCRIPTION

As will be described in detail hereinafter, various embodiments of a system and method for measuring phase fractions in a multi-phase fluid are presented.

For purposes of this application and invention, there are various definitions that are germane. The term 'microwave frequency range' is used to refer to electromagnetic frequencies between hundreds of MHz to several hundreds of GHz. Furthermore, the term 'multi-phase,' as used herein, is used to refer to a composition that includes at least two phases of materials. The multi-phase fluid may include some combination of oil, water, and gas. For example, the fluid may include gas and water. In one example, the water may be saline water. In another example, the fluid may include gas and oil. The term 'conduit,' as used herein, refers to any structure that permits a flow of the multi-phase fluid. Further, the term conduit is not limited to elements that have a substantially circular cross-section, are substantially closed, or are longitudinal elements.

In accordance with aspects of present disclosure, phase fractions of phases in a multi-phase fluid are measured using one or more sensing devices operating in the microwave frequency range. The sensing devices include at least one antenna, one or more substrates and one or more dielectric layers. Further, sensing devices may either be transmitting sensing devices or receiving sensing devices or a combination of both. The term 'antenna,' as used herein, may be used to refer to a transmitting and/or receiving element that is capable of operating at microwave frequencies. The antenna may include one or more metal portions over a ground plane, where the one or more metal portions and the ground plane are separated by one or more substrates. In various embodiments, the sensing devices are fixed on a surface of a conduit that is configured to carry the multi-phase fluid such that the dielectric layer is in direct contact with the multi-phase fluid while shielding the antenna from direct contact with the multi-phase fluid. The sensing devices may be inserted into an open space of the conduit through one of the conduit walls or placed on an inner surface of the walls of the conduit to allow for the multi-phase fluid to be in direct contact with the sensing device. For example, in the case of a metallic conduit, the sensing devices may be disposed on the inner surface of the conduit, whereas in the case of a non-metallic conduit, the sensing device may be disposed on the outer surface of the conduit utilizing an external mounting mechanism, such as a strap-on mechanism. In one embodiment, the substrates may be flexible, thereby allowing the substrates to conform to a conduit surface. Moreover, the antenna substrates may be designed in such a manner to ensure that the flow of the multi-phase fluid through the conduit is not disturbed. In one example, the antenna may include a microstrip patch. The microstrip patch is representative of a metal patch that is printed, for example, onto the dielectric layer. Microstrip patches have the advantage of being lightweight, inexpensive and easy to integrate with other electronics.

In one embodiment, the antennas in the sensing devices emit electromagnetic waves of a range of frequencies and the transmitted or reflected electromagnetic waves are measured over that frequency range. For a given conduit diameter, the resonant frequency of a system including the conduit and the multi-phase fluid, depends on the permittivity (dielectric constant) of the multi-phase fluid inside the conduit. The dielectric constant is a complex property including a real part and an imaginary part. The dielectric constant of the multi-phase fluid can cause the transmitted or reflected electromagnetic waves to display properties, which can be measured in the form of resonant frequencies observed in the transmitted or reflected electromagnetic waves, amplitude and phase angle of the transmitted or reflected electromagnetic waves at the resonant frequencies, and a quality (Q) factor of the transmitted or reflected electromagnetic waves at the resonant frequencies. The Q factor may be a ratio between a center frequency of the transmitted or reflected response and a corresponding frequency bandwidth of the transmitted or reflected response. A difference between resonant frequencies based on the permittivity of the medium inside the conduit may be used to estimate the phase fraction of the multi-phase fluid. In addition, the quality factor (Q) of the transmitted or reflected waves and the amplitude of the transmitted or reflected waves at the resonant frequencies can also be used to estimate the phase fraction of the multi-phase fluid. The resonant frequency is related to permittivity. The sharpness of the resonance peaks in the transmitted or reflected waves, which is quantified by the Q factor, and amplitude are inversely proportional to the imaginary part of the dielectric constant. For instance, as the water content within the multi-phase fluid increases, the effective dielectric constant increases and the resonant frequency decreases. Similarly, if the water is lossy, e.g., due to salinity, that will result in a decrease in the peak amplitude and an increase in the width of the peak. In accordance with embodiments of the present invention, the sensing device described herein is configured to produce resonance in the multi-phase fluid even when the fluid is lossy.

Figure 1:
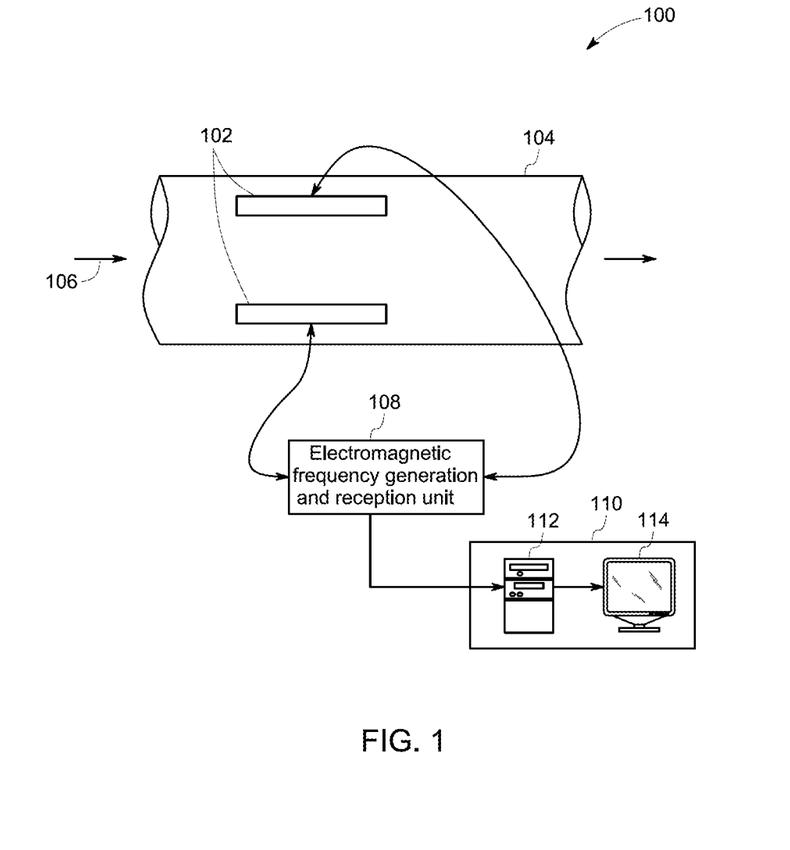
FIG. 1 is a diagrammatical representation of a multi-phase flow measurement system using at least one sensing device.

FIG. 1 depicts a diagrammatical representation of a phase flow measurement system 100 including one or more sensing devices 102. Each sensing device 102 includes an antenna that is configured to emit electromagnetic waves in the microwave frequency range. The sensing devices 102 may be disposed on a conduit 104. In particular, the sensing devices 102 may be placed in close proximity to a multi-phase fluid 106 flowing through the conduit 104. The multi-phase fluid may include fractions of different phases such as oil, water, and gas. Based on the phase that has a major contribution in the multi-phase fluid, the multi-phase fluid flow state may be categorized as an oil-continuous flow state or a water-continuous flow state. In the oil-continuous flow state, the multi-phase fluid 106 includes substantial portions of oil in comparison with water and/or gas. Whereas, in the water-continuous state, the multi-phase fluid 106 includes substantial portions of water in comparison with oil and/or gas.

The sensing devices 102 may be excited to cause the antennas to emit electromagnetic waves of a range of frequencies. The range of frequencies may include a range of microwave frequencies. By way of example, the range of frequencies may range from about 300 MHz to about 300 GHz.

The system 100 may also include an electromagnetic frequency generation and reception (EMFGR) unit 108. The EMFGR unit 108 may be configured to cause the one or more sensing devices 102 to emit electromagnetic waves of the desired range of frequencies. The EMFGR unit 108 may include an electronic device. In one example, the electronic device may include a vector network analyzer (VNA). Furthermore, the EMFGR unit 108 may be operatively coupled to a controller 110. The controller 110 may be programmable logic controller (PLC) or programmable automation controller (PAC). The controller 110 may include a graphical user interface 114 and a processing unit 112 that may be configured to control the operations of the EMFGR unit 108. In one example, the graphical user interface 114 may include a display unit. In one example, the graphical user interface 114 may be configured to display the data processed by the processing unit 112.

The antennas from the sensing devices 102 and the multi-phase fluid 106 in the conduit 104 may be represented as an electrical network that has a plurality of ports that interact with each other. The electrical network may be represented as a two-port network and may be analyzed using S-parameters. The ports are points at which electrical signals either enter and/or exit the electrical network. In the system 100, the ports are the one or more antennas through which electromagnetic waves enter the multi-phase fluid 106 and also through which transmitted or reflected electromagnetic waves are collected. The S-parameter may be represented by a unit-less complex number that represents a magnitude and an angle, such as amplitude and a phase angle of the transmitted or reflected electromagnetic waves. A two-port electrical network may be represented by the S-parameters S11, S12, S21, and S22. For example, S11 parameters represent amplitude and phase angle at a given frequency associated with each reflected electromagnetic wave received at a first port in response to incident electromagnetic waves emitted by the first port. Similarly, S12 parameters represent amplitude and phase angle at a particular frequency associated with each reflected electromagnetic wave received at the first port in response to incident electromagnetic waves emitted by a second port. Moreover, S21 parameters are associated with electromagnetic waves received at the second port in response to incident electromagnetic waves emitted by the first port, while S22 represents parameters associated with electromagnetic waves received at the second port in response to incident electromagnetic waves emitted by the second port.

In the system 100, the two ports of the electrical network may correspond to the ports of the sensing devices 102 that are coupled to the EMFGR unit 108. The sensing devices 102 may be excited to emit electromagnetic waves of the range of frequencies via use of an incident signal generated by the EMFGR unit 108. The incident signal is representative of a signal which is provided as an input to a port associated with one of the sensing devices 102 by the EMFGR unit 108. The electromagnetic waves emitted by one of the sensing devices 102 may either be transmitted to an opposite end of the conduit 104 and received by another of the sensing devices 102 or may be reflected and received by the transmitting sensing device 102. Accordingly, transmitted and/or reflected electromagnetic waves may be acquired at one of the ports. The term 'transmitted' and 'reflected' electromagnetic waves as used herein may be used to refer to transmitted/reflected electrical signals. Such electrical signals may be measured using at least one of a voltage value, a current value, and a power value. The electronic device of the EMFGR unit 108 may be configured to measure S-parameters corresponding to the transmitted or reflected electromagnetic waves received at the ports. The controller 110 may be configured to determine the amplitude and the phase angle corresponding to the transmitted or reflected electromagnetic waves based on the S-parameters.

Further, for an oil-continuous flow state, the controller 110 may be employed to determine the phase fraction of phases (viz. oil, gas, and water) in the multi-phase fluid based on the amplitude, and the phase angle of the transmitted or reflected electromagnetic waves. In one example, determining the fraction of each phase of the multi-phase fluid may entail determining a water fraction, gas fraction, and an oil fraction of the multi-phase fluid. The term 'water cut' is used to refer to a water volume flow rate relative to the total liquid volume flow rate (oil and water) at standard pressure and temperature. Also, the term 'gas volume fraction' (GVF) is used to refer to a parameter which provides a measure of a quantity of gas present in a multi-phase fluid. In particular, the GVF refers to a gas volume flow rate relative to the multi-phase fluid volume flow rate at a pressure and temperature prevailing in a measurement environment. Both the water cut and the GVF are usually expressed as percentages.

Although the multi-phase flow measurement system 100 may be able to determine phase fractions for a multi-phase fluid in an oil-continuous flow state, it may not be able to determine phase fractions for a multi-phase fluid in the water-continuous flow state. The electromagnetic waves emitted by the sensing devices 102 may be attenuated while travelling through the water-continuous multi-phase fluid. The attenuation may lead to a reduction in the Q-factor at resonant frequencies in the transmitted or reflected electromagnetic waves. In accordance with embodiments of the invention, the system illustrated in FIG. 2 is configured to provide resonance even in lossy media, such as water-continuous multi-phase fluid.

Figure 2:
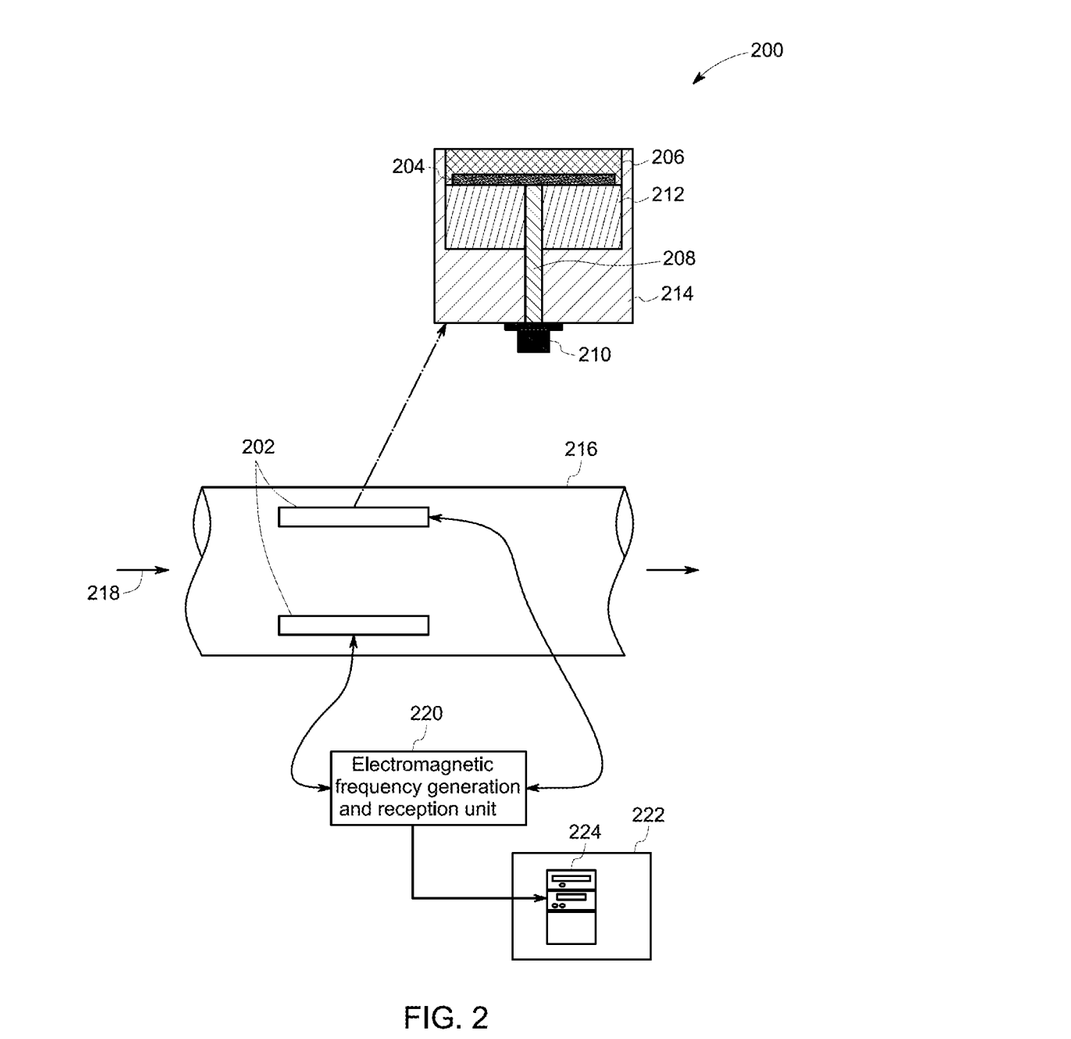
FIG. 2 is diagrammatical representation of a sensing system for determination of phase fractions in a multi-phase fluid placed proximate to a conduit, in accordance with an embodiment of the present invention.

FIG. 2 is diagrammatical representation of a multi-phase measurement system 200 including a sensing device 202 for determination of phase fractions in a water-continuous multi-phase fluid, in accordance with an embodiment of the present invention. The sensing device 202 is placed proximate to the conduit 216 that carries a multi-phase fluid 218. The sensing device 202 includes an antenna 204, a dielectric layer 206, a feeding element 208, a connector 210, a substrate 212, and a metallic enclosure 214.

The antenna 204 is configured to emit electromagnetic waves of a range of frequencies into the multi-phase fluid flowing through the conduit 216. Examples of antenna 204 include, but are not limited to, a patch antenna, a monopole antenna, a dipole antenna, and a multi-pole antenna. In the sensing device 202, the antenna 204 is placed on a substrate 212. In certain examples, the substrate may be manufactured from flexible material such as silicone, plastic, woven natural fibers, and other suitable polymers, copolymers, and combinations thereof. The material for the substrate 212 may be selected such that the sensing device 202 is flexible in nature while being able to sustain high pressure and temperature. The antenna 204 may be coupled to the substrate 212 with adhesive means. In other embodiments, the antenna 204 may be printed onto the substrate 212 as a thin metallic strip. Further, the antenna 204 is selected such that the resonance is observed in the transmitted or reflected electromagnetic waves in a first set of frequencies based on the flow state of the multi-phase fluid.

Further, the dielectric layer 206 from the sensing device 202 is placed over a surface of the antenna 204 such that the dielectric layer acts as a barrier between the antenna and the multi-phase fluid 218. The dielectric layer 206 may be placed on or over the antenna 204 or the antenna 204 may be printed on the dielectric layer 206 or embedded into the dielectric layer 206 such that the antenna may be covered by the dielectric layer 206. The dielectric layer 206, according to certain embodiments, is made from material that leads to minimum attenuation of the electromagnetic waves emitted by the antenna 204. Further, the dielectric layer 206 may be made from material that is flexible in nature to allow for the layer 206 to conform to the inner surface of the conduit 216 when the sensing device 202 is fitted on the conduit 216. In certain examples, the dielectric layer 206 can be fabricated using hard materials to conform to the inner surface of the conduit 216. Examples of materials that can be used to make the dielectric layer 206 include, but are not limited to, polyetheretherketone (PEEK), silicone, PTFE-coated fabric, epoxy resin, fiberglass etc. The dielectric layer 206 may be shaped in accordance with the shape of the antenna 204. For example, when the antenna 204 is rectangular in shape, the dielectric layer 206 may also be rectangular in shape. The dielectric layer 206 is designed such that the transmitted or reflected electromagnetic waves from the multi-phase fluid in the conduit 216 exhibit resonances in at least one of the first set of frequencies and a second set of frequencies based on a flow state of the multi-phase fluid. In order to set resonance at the first and second set of frequencies for different flow states, design considerations of the dielectric layer 206 include a type of material of the dielectric layer, a circumference of the surface of the layer that is in direct contact with the multi-phase fluid, and a thickness of the dielectric layer 206.

The sensing device 202 also includes a feed element 208 that is coupled to the antenna 204. The feed element 208 may be a coaxial cable that is coupled to the RF connector 210. The RF connector 210, in turn, may be coupled to the EMFGR unit 220. The feed element 208, based on the signals from the controller 222, provides excitation energy to excite the antenna 204 and cause electromagnetic waves of a range of frequencies to be emitted into the multi-phase fluid. In certain embodiments, the feed element 208 may include a coaxial cable and a metal element (not shown). The metal element may be placed on an additional substrate (not shown) that is coupled to the substrate 212. The coaxial cable of the feed element 208 may be coupled to the metal element on one end and the RF connector 210 on the other end. In such a case, the feed element 208 may be coupled to the antenna 204 through an aperture defined in the substrate 212 and the additional substrate.

Further, the antenna 204, dielectric layer 206, feed element 208, and substrate 212 are inserted into the metallic enclosure 214. The metallic enclosure 214 is placed such that at least one surface of the dielectric layer 206 is uncovered. The uncovered surface of the dielectric layer 206 is placed on the conduit 216 such that it is in direct contact with the multi-phase fluid 218 in the conduit 216.

In operation, a plurality of sensing devices 202 are placed along the circumference of the conduit 216 to measure various parameters of the multi-phase fluid 218 flowing in the conduit 216. The EMFGR unit 220 receives an input from the controller 222 to excite the sensing devices 202 with appropriate amount of power so that at least one of the antennas 204 coupled to the EMFGR unit 220 emits electromagnetic waves of a range of frequencies that include the first set of frequencies and the second set of frequencies. The antennas 204 emit electromagnetic waves that are directed to the fluid 218 through the dielectric layer 206. Further, the sensing devices 202 are configured to receive transmitted or reflected electromagnetic waves from the multi-phase fluid in the conduit 216.

The transmitted or reflected electromagnetic waves that are received by the sensing devices 202 are communicated to the controller 222 through the EMFGR unit 220. A processing unit 224, which is part of the controller 222, is configured to determine a plurality of parameters related to the transmitted or reflected electromagnetic waves. The processing unit 224 is also configured to determine a classification parameter for the multi-phase fluid 218. The classification parameter is determined based on analysis of the transmitted or reflected electromagnetic waves in at least one of the first set of frequencies and the second set of frequencies. In an embodiment, the presence of resonance in the second set of frequencies is utilized to determine the flow state of the multi-phase fluid 218. Further, amplitude of the transmitted or reflected electromagnetic waves in the first set of frequencies may also be utilized to determine the flow state of the multi-phase fluid 218. Further, the processing unit 224 is configured to select a fraction determination model based on the flow state of the multi-phase fluid 218. The fraction determination model can be used to determine the phase fractions of the multi-phase fluid 218 in the conduit 216.

The processing unit 224, in certain embodiments, may comprise one or more central processing units (CPU) such as a microprocessor, or may comprise any suitable number of application specific integrated circuits working in cooperation to accomplish the functions of a CPU. The processing unit 224 may include a memory. The memory can be an electronic, a magnetic, an optical, an electromagnetic, or an infrared system, apparatus, or device. Common forms of memory include hard disks, magnetic tape, Random Access Memory (RAM), a Programmable Read Only Memory (PROM), and EEPROM, or an optical storage device such as a re-writeable CDROM or DVD, for example. The processing unit 224 is capable of executing program instructions, related to the determination of phase fractions in the multi-phase fluid, and functioning in response to those instructions or other activities that may occur in the course of or after determining phase fractions. Such program instructions will comprise a listing of executable instructions for implementing logical functions. The listing can be embodied in any computer-readable medium for use by or in connection with a computer-based system that can retrieve, process, and execute the instructions. Alternatively, some or all of the processing may be performed remotely by additional processing units 224. The controller 222, specifically the processing unit 224 in the controller 222, may perform operations implemented in the form of models such as those that are required to determine phase fractions, or those required to determine permittivity values as described herein.

According to one embodiment, the parameters determined by the processing unit 224 include, but are not limited to, one or more resonant frequencies of the transmitted or reflected electromagnetic waves, amplitude of the transmitted or reflected electromagnetic waves at the one or more resonant frequencies, the phase angle of the transmitted or reflected electromagnetic waves and a group delay of the transmitted or reflected electromagnetic waves. Group delay of the transmitted or reflected electromagnetic waves may be determined known methods. One such method has been described in the commonly assigned U.S. patent application Ser. No. 14/294,215 titled "MULTIPHASE FLOW MEASUREMENT USING ELECTROMAGNETIC SENSORS".

Further, the controller 222, based on the parameters determined, is configured to determine if the one or more resonant frequencies observed in the transmitted or reflected electromagnetic waves include frequencies from the first set of frequencies and the second set of frequencies. The controller 222, according to one embodiment, is configured to select a water-continuous flow state as the flow state of the multi-phase fluid in the conduit 216 when the one or more resonant frequencies of the transmitted or reflected electromagnetic waves include frequencies, among others, from the first set of frequencies alone. The controller 222, according to another embodiment, is configured to select an oil-continuous flow state as the flow state of the multi-phase fluid in the conduit 216 when the one or more resonant frequencies of the transmitted or reflected electromagnetic waves include frequencies, among others, from the first set as well as the second set of frequencies.

Further, the controller 222 is configured to determine permittivity (εm) of the multi-phase fluid from the conduit 216 based on the one or more parameters determined from the transmitted or reflected electromagnetic waves received by the sensing devices 202. In one embodiment, one or more of the parameters such as amplitude, the phase angle, and the resonant frequencies corresponding to the transmitted or reflected electromagnetic waves may be processed using regression analysis to obtain a transfer function that relates these parameters to the permittivity of the multi-phase fluid. Accordingly, the permittivity of the multi-phase fluid inside the conduit 216 may be determined based on one or more of the amplitude, phase angle, group delay and resonant frequencies of the transmitted or reflected electromagnetic waves. Permittivity of the multi-phase fluid 218 may also be determined using an observed shift in the resonant frequencies. A shift in resonant frequencies is proportional to the permittivity of the multi-phase fluid. εm may comprise two major components: permittivity of the water phase in the multi-phase fluid (εw) and permittivity of the oil components in the multi-phase fluid (εo).

The permittivity of water phase may be determined by the controller 222 using known models such as the Stogryn model. The Stogryn model gives the permittivity of water phase of the fluid as a function of temperature of the fluid and salinity of the fluid. Temperature and salinity may be determined by using other sensing mechanisms such as near field probes, temperature gauges and the like.

According to an embodiment, the permittivity of oil may be dependent on a density of the oil present in the multi-phase fluid. The density of oil and permittivity (εm) of the multi-phase fluid may be translated to the permittivity (εo) of oil phase using models such as the Claussius-Mossotti Model.

Furthermore, the controller 222 is configured to determine the phase fractions in the fluid using at least one fraction determination model that utilizes the permittivity of the multi-phase fluid, permittivity of water phase, and the permittivity of oil phase. Examples of a fraction determination model are represented as Equations 1 and 2. Equations 1 and 2 are known as Bruggeman equations that are used to determine phase fractions based on permittivity.

$$WC = 1 - \frac{\varepsilon_m - \varepsilon_w}{\varepsilon_0 - \varepsilon_w} \times \left(\frac{\varepsilon_o}{\varepsilon_m}\right)^{1/3} \tag{1}$$

WC is the phase fraction of the water phase in the multi-phase fluid, $\varepsilon_m$ is the permittivity of the multi-phase fluid, $\varepsilon_w$ is the permittivity of water phase of the multi-phase fluid, and $\varepsilon_o$ is the permittivity of oil phase of the multi-phase fluid.

For water continuous phase, the permittivity of the oil phase and the permittivity of the multi-phase fluid may be used in a fraction determination model, such as the fraction determination model represented by equation 2, to determine phase fractions in the multi-phase fluid.

$$WC = \frac{\varepsilon_m - \varepsilon_o}{\varepsilon_w - \varepsilon_o} \times \left(\frac{\varepsilon_w}{\varepsilon_m}\right)^{1/3} \tag{2}$$

WC is the phase fraction of the water phase in the multi-phase fluid, $\varepsilon_m$ is the permittivity of the multi-phase fluid, $\varepsilon_w$ is the permittivity of water phase of the multi-phase fluid, and $\varepsilon_o$ is the permittivity of oil phase of the multi-phase fluid.

According to another embodiment, the phase fractions may also be calculated by applying transfer functions, such as Maxwell Garnet, and the like.

According to yet another embodiment, fraction determination models for oil-continuous type multi-phase fluid in the conduit may be a transfer function that relates the permittivity of the multi-phase fluid and that of the oil phase and water phase with the oil phase fraction in the multi-phase fluid. Further, the fraction determination models may also be dependent on other parameters of the multi-phase fluid such as salinity, temperature etc. Similarly, for water-continuous type multi-phase fluid 218 in the conduit 216, the fraction determination model may be a transfer function that relates the determined permittivity of the fluid with the water phase fraction in the multi-phase fluid.

To transmit electromagnetic waves into the multi-phase fluid and to gather reflected electromagnetic waves from the multi-phase fluid, the sensing device 202 may be placed proximate to the conduit 216 in various ways. Some configurations of sensing device placement techniques have been diagrammatically represented in FIGS. 3 and 4.

Figure 3:
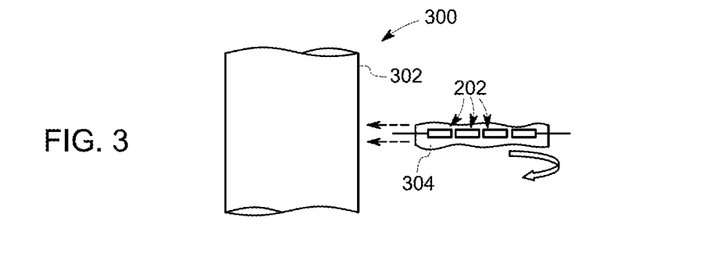
FIGS. 3-4 are diagrammatical representations of various exemplary sensing device configurations of the system of FIG. 2, in accordance with embodiments of the present invention.

FIG. 3 is a diagrammatical representation 300 of an embodiment of a configuration of the sensing devices 202. This representation of the configuration of sensing devices 202 includes a conduit 302 and a strap-on device 304. The strap-on device 304 may include a plurality of sensing devices 202 disposed thereon. Furthermore, the strap-on device 304 may be configured to be installed around an outer surface of the conduit 302. In one example, the strap-on device 304 may be wrapped around the conduit 302. The strap-on device 304 may be made of any suitable material that allows the strap-on device 304 to adequately flex around the circumference of the conduit 302. Typically, the strap-on device 304 may be employed in situations where the conduit 302 is non-metallic (for example, plastic, glass, ceramic, and the like) or has sections that are non-metallic. Creating apertures in non-metallic conduits and fixing the sensing device 202 with commercial adhesives in the apertures may not tightly couple the sensing device 202 and the walls of the conduit 302. The strap-on device 304 may be installed with non-metallic conduits since it eliminates the need of drilling, soldering, using adhesives. The elimination of these activities in the case of non-metallic conduits reduces the risk of breakage of such conduits. The strap-on device 304 having the plurality of sensing devices 202 disposed thereon may be installed along a portion of the conduit 302. The plurality of sensing devices 202 may be configured in a substantially linear arrangement so that the plurality of sensing devices 202 substantially surrounds the conduit 302 when the strap-on device 304 is attached to the conduit 302. The strap-on device 304 may also be installed around a new conduit 302 prior to use or installed around an existing conduit 302 (for example, during temporary shutdown), thereby offering a retrofit solution.

Figure 4:
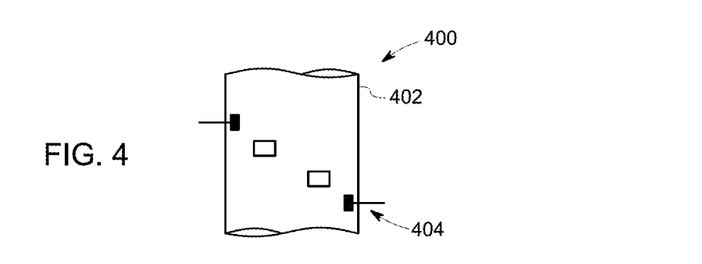

Turning now to FIG. 4, a diagrammatical representation 400 of another embodiment of a configuration of sensing devices is presented. The sensing device configuration 400 in the embodiment of FIG. 4 includes a helical configuration. The configuration 400 may include a conduit 402 and a plurality of sensing devices 404 arranged in a substantially helical arrangement. The plurality of sensing devices 404 may be configured to substantially surround the circumference of the conduit 402. The helical arrangement of sensing devices 404 may be used, for example, on an inside surface of a metallic conduit 402. In another example, the helical patch configuration of the sensing devices 404 may be used on an outside surface of a non-metallic conduit 402. In yet another example, the helical patch configuration of the sensing devices 404 may be used on a conduit which has sections that are non-metallic. The helical patch configuration may be installed within a new conduit 402 or on the new conduit 402 prior to use. In one example, the helical patch configuration may be installed in or on an existing conduit 402 (for example, during temporary shutdown), thereby offering a retrofit solution. Clearly, other embodiments and configurations of sensing devices may be used without departing from the scope of the present disclosure.

Figure 5:
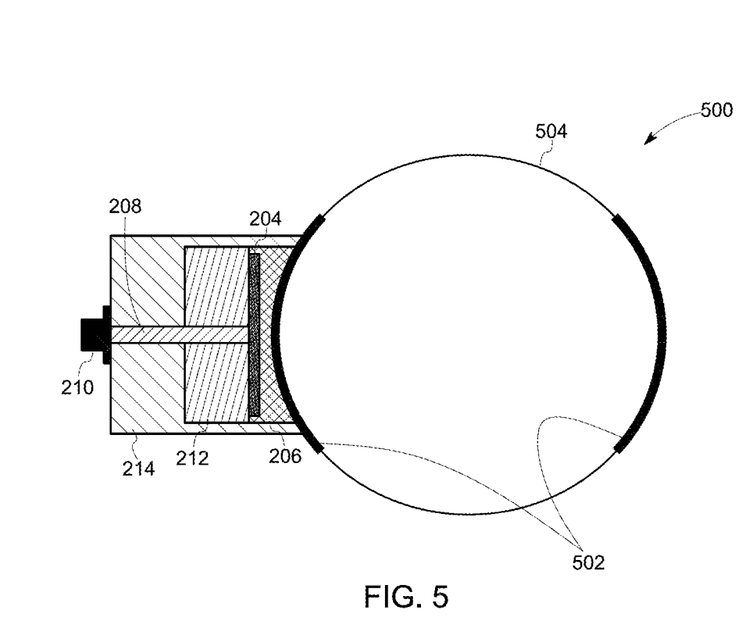
FIG. 5 is a diagrammatical representation of cross-sectional view of portion of the conduit using the sensing device of FIGS. 3-4, in accordance with embodiments of the present invention.

FIG. 5 depicts a cross-sectional view of a conduit having one or more sensing devices. The conduit may be representative of the conduit 216 of FIG. 2, while the sensing devices may be representative of the sensing device 202 of FIG. 2. As illustrated in FIG. 5, the sensing device 202 include a dielectric layer 206 designed to conform to the shape (for example, curved) of the conduit 504. The dielectric layer 206 is fitted along the area 502 of the conduit 504 such that the surface of the dielectric layer 206 that occupies the area 502 is in-line with the rest of the inner surface of the conduit 504. This embodiment allows close or exact conformance between the shape of the sensing devices and the conduit 504.

In various embodiments, a shape of the antenna from the sensing device 202 of FIG. 2 may vary. The shape of the sensing device 202 in FIG. 2 may be a function of the shape used for the antennas 204 in the sensing device 202. The shape of the antenna may form virtually any polygonal shape or combinations thereof. For example, the antenna 204 may be rectangular in shape. A long axis of the rectangular antenna may be oriented in a plane perpendicular to a conduit axis or along the conduit axis. The long axis is representative of the axis of the antenna along the length of the rectangular antenna. In another example, the antenna may have a square shape, as well as, an elliptical shape.

In additional examples, the antenna may have a circular shape. Further, in another example, an antenna may have a ring shape. Similarly, in addition to the physical shape of the antennas, antennas with different polarizations may be used. For example, the polarization of the antennas may be elliptical, circular, linear, and the like. Use of antennas having other shapes and polarizations is also contemplated.

Figure 6:
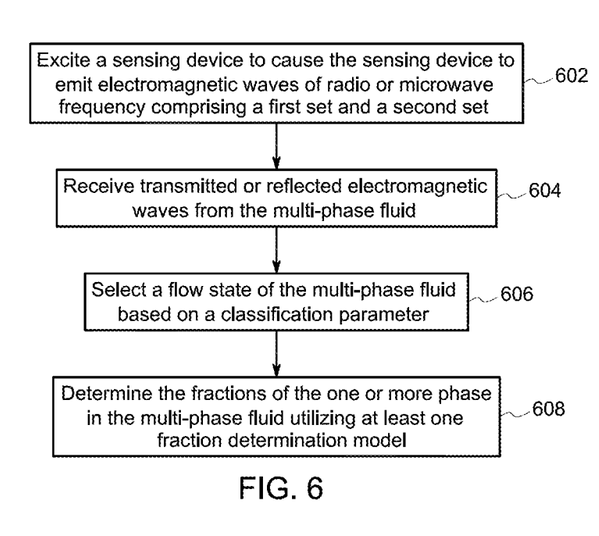
FIG. 6 is a flow chart representing a method for determining phase fractions in a multi-phase fluid, in accordance with an embodiment of the present invention.

FIG. 6 illustrates a flow diagram of a method of determination of phase fractions of a multi-phase fluid. The illustrated method, according to one embodiment, can be utilized to determine phase fractions of the one or more phases in the multi-phase fluid 218 flowing in the conduit 216 of FIG. 2. To determine phase fractions, a sensing device (for example: sensing device 202) is placed proximate to the multi-phase fluid. The sensing device, as described along with FIG. 2, includes an antenna 204 and a dielectric layer 206.

The method includes, at step 602, exciting the sensing device to cause the sensing device to emit electromagnetic waves of a range of frequencies into the multi-phase fluid. The range of frequencies includes a first set of frequencies and a second set of frequencies. The electromagnetic waves may be emitted into the multi-phase fluid sequentially. As described along with FIG. 2, the sensing device is selected such that resonance may be observed in the first set of frequencies. Further, the dielectric layer on the sensing device is selected such that, based on a flow state of the multi-phase fluid, resonance may be observed in the second set of frequencies. Further, the method includes, receiving (604) transmitted or reflected electromagnetic waves from the multi-phase fluid. The transmitted or reflected electromagnetic waves may be received by one of the ports associated with the sensing device. The transmitted or reflected electromagnetic waves are transferred to the controller, such as the controller 222, for further processing required to determine the phase fractions of the fluid.

At step 606, the flow state of the multi-phase fluid is selected based on a classification parameter. The classification parameter is determined based on an analysis of the transmitted or reflected electromagnetic waves. In one embodiment, the analysis may include determining resonant frequencies in the transmitted or reflected electromagnetic waves. Further, determining the classification parameter may also include determining if the resonant frequencies include frequencies from the first set of frequencies and the second set of frequencies. In one embodiment, the flow state of the multi-phase fluid is determined to be water continuous if the resonant frequencies in the transmitted or reflected electromagnetic waves include, among others, frequencies only from the first set of frequencies. Similarly, the flow state of the multi-phase fluid is determined to be oil continuous if the resonant frequencies in the transmitted or reflected electromagnetic waves include, among others, frequencies from the first set of frequencies as well as the second set of frequencies.

At 608, the method includes determining the phase fractions of the one or more phases in the multi-phase fluid utilizing at least one fraction determination model. The fraction determination model is selected based on the flow state of the multi-phase fluid. As described in conjunction with FIG. 2, phase fractions for an oil-continuous multi-phase fluid may be determined using Equation 1. Similarly, phase fractions for a water-continuous multi-phase fluid may be determined using Equation 2.

The fraction determination models utilize one or more parameters associated with the transmitted or reflected electromagnetic waves. S-parameters associated with the transmitted or reflected electromagnetic waves may be measured at one of the ports of the sensing device. Further, the controller may determine the one or more parameters associated with the transmitted or reflected electromagnetic waves from the S-parameters. Examples of the one or more parameters include, but are not limited to, one or more resonant frequencies observed in the transmitted or reflected waves, amplitude of the transmitted or reflected electromagnetic waves at the one or more resonant frequencies, phase angle of the waves at the one or more resonant frequencies.

The fraction determination models utilize permittivity ($\varepsilon m$) of the multi-phase fluid, permittivity ($\varepsilon w$) of the water phase in the multi-phase fluid, and permittivity ($\varepsilon o$) of the oil-phase in the multi-phase fluid. According to one embodiment, permittivity values are determined utilizing the one or more parameters determined from the transmitted or reflected electromagnetic waves.

The fraction determination models may also utilize one or more characteristics of the multi-phase fluid for determination of phase fractions. The one or more characteristics include, but are not limited to, salinity, temperature, and pressure of the multi-phase fluid in the conduit. These characteristics may be determined using one or more sensing mechanisms such as near field probes, temperature gauges, pressure sensors, and the like.

Figure 7:
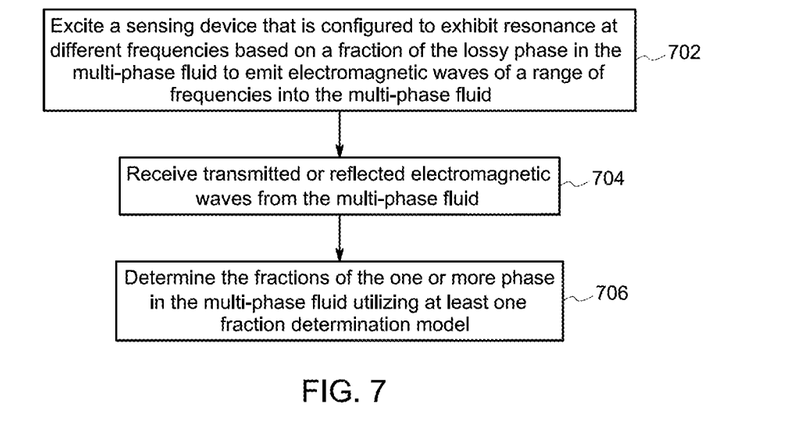
FIG. 7 is a flow chart representing a method for determining phase fractions in a multi-phase fluid, in accordance with another embodiment of the present invention.

FIG. 7 illustrates a flow diagram of a method of determination of phase fractions of a multi-phase fluid. The illustrated method, according to one embodiment, can be utilized to determine phase fractions of the one or more phases in the multi-phase fluid 218 flowing in the conduit 216 of FIG. 2. The multi-phase fluid 218 may include substantial portions of a lossy phase among the one or more phases. Examples of lossy phase include, but are not limited to, water, water that includes salts and other minerals, and the like. According to one embodiment, a flow state of the multi-phase fluid with a lossy phase may be water continuous. To determine phase fractions, a sensing device (for example: sensing device 202) is placed proximate to the multi-phase fluid. The sensing device, as described along with FIG. 2, includes an antenna 204 and a dielectric layer 206. The antenna 204 and the dielectric layer 206 are selected such that resonance is exhibited at different frequencies based on a fraction of the lossy phase in the multi-phase fluid.

The method includes, at step 702, exciting the sensing device to cause the sensing device to emit electromagnetic waves of a range of frequencies into the multi-phase fluid. The electromagnetic waves may be emitted into the multi-phase fluid sequentially. Further, the method includes, receiving (704) transmitted or reflected electromagnetic waves from the multi-phase fluid. The transmitted or reflected electromagnetic waves may be received by one of the ports associated with the sensing devices coupled to the conduit 216. The transmitted or reflected electromagnetic waves are transferred to the controller, such as the controller 222, for further processing required to determine the phase fractions of the fluid.

At step 706, phase fractions of the one or more phases, including the lossy phase, in the multi-phase fluid are determined utilizing at least one fraction determination model. As described in conjunction with FIG. 2, phase fractions for a water-continuous multi-phase fluid, which includes water or saline water in substantial portions, may be determined using Equation 2.

The fraction determination models utilize one or more parameters associated with the transmitted or reflected electromagnetic waves. S-parameters associated with the transmitted or reflected electromagnetic waves may be measured at one of the ports of the sensing device. Further, the controller may determine the one or more parameters associated with the transmitted or reflected electromagnetic waves from the S-parameters. Examples of the one or more parameters include, but are not limited to, one or more resonant frequencies observed in the transmitted or reflected waves, amplitude of the transmitted or reflected electromagnetic waves at the one or more resonant frequencies, phase angle of the waves at the one or more resonant frequencies.

The fraction determination models utilize permittivity ($\varepsilon m$) of the multi-phase fluid, permittivity ($\varepsilon w$) of the water phase in the multi-phase fluid, and permittivity ($\varepsilon o$) of the oil-phase in the multi-phase fluid. According to one embodiment, permittivity values are determined utilizing the one or more parameters determined from the transmitted or reflected electromagnetic waves.

The fraction determination models may also utilize one or more characteristics of the multi-phase fluid for determination of phase fractions. The one or more characteristics include, but are not limited to, salinity, temperature, and pressure of the multi-phase fluid 218 in the conduit 216. These characteristics may be determined using one or more sensing mechanisms such as near field probes, temperature gauges, pressure sensors, and the like.

Figure 8:
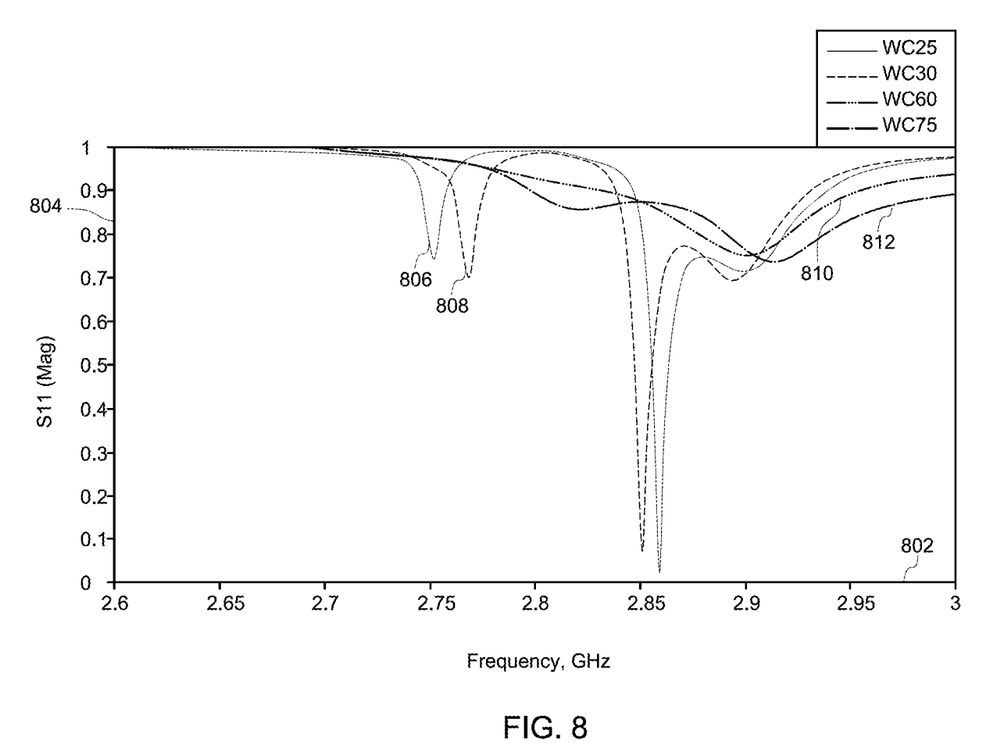
FIG. 8 is a graphical representation depicting a relationship between frequency of the electromagnetic waves and magnitude of the reflected electromagnetic waves, according an embodiment of the present invention.

FIG. 8 is a graphical representation depicting a relationship between frequencies of electromagnetic waves emitted by the sensing device 202 and amplitudes of the S11 parameters of reflected electromagnetic waves collected by the sensing device 202, according an embodiment of the present invention.

The one or more frequencies from the range of frequencies are plotted on the frequency axis 802. Further, a magnitude of the reflected waves (S11) received by the sensing device 202 is plotted on the Y-axis 804. In the graphical representation, the value of magnitude lies between 0 and 1. A value of 0 represents that there was no reflection and all the incident power was transmitted into the fluid. On the other hand, a value of 1 indicates that that all of the incident power was reflected back. In the current representation, a value closer to 0 indicates resonance.

The graphical representation includes a plurality of plot lines, such as plot lines 806, 808, 810, and 812 for different multi-phase fluid samples used in the experimental setup. Different multi-phase fluid samples were selected based on a known value of fraction of water phase in the fluid. In the illustrated example, line 806 represents a response received from multi-phase fluid with water content at 25%. Similarly, line 808 represents a response received from multi-phase fluid with water content at 30%, line 810 represents response from multi-phase fluid with water content at 60%, and line 812 represents response from multi-phase fluid with water content at 75%.

In plot line 806, the magnitude of power of reflected waves received by the sensing devices is at a minimum at a frequency in the range of approximately 2.7 GHz-2.8 GHz. Further, the plot line shows that the magnitude dips to a low value again at frequencies in the range of ~2.85 GHz-3 GHz. Resonance is thus observed in a first set of frequencies (falling in the 2.853-3 GHz range) and a second set of frequencies (2.7 GHz 2.8 GHz). Similarly in the plot line 808, resonance can be observed at ~2.77 GHz as well as in the range ~2.85 GHz-3 GHz. However, in plot line 810, the resonance is observed in the first set of frequencies. Similarly, in the plot line 812, the resonance observed at the second set of frequencies is weak whereas the resonance in the first set of frequencies is stronger.

From the observation of weak and strong resonances at the first set and second set of frequencies for different fluid samples, it can be concluded that with the use of sensing devices that include antennas and dielectric layers fluids can be categorized based on their flow state. The categorization helps in selecting the fraction determination model to determine the phase fractions in the multi-phase fluid.

Various embodiments described above thus provide for a system and a method for determining phase fractions in a multi-phase fluid. The above-described embodiments of the system and method provide for an inexpensive way of determining phase fractions in both water-continuous as well as oil-continuous fluids. Further, the conduit conforming design of the dielectric layer makes it possible for non-intrusive measurements at actual conduit locations. The sensing device, owing to its broadband frequency operational range, provides for increased accuracy in determination of phase fractions.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of ordinary skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," etc. are used merely as labels, and are not intended to impose numerical or positional requirements on their objects.

This written description uses examples to disclose several embodiments of the invention, including the best mode, and also to enable any person of ordinary skill in the art to practice the embodiments of invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described method and system for determining phase fractions of a multi-phase fluid, without departing from the spirit and scope of the invention herein involved, it is intended that all of the subject matter of the above description or shown in the accompanying drawings shall be interpreted merely as examples illustrating the inventive concept herein and shall not be construed as limiting the invention.

The invention claimed is:

1. A method of determining a fraction of one or more phases in a multi-phase fluid in a conduit, comprising:
    exciting a sensing device to cause the sensing device to emit electromagnetic waves of a range of frequencies comprising a first set of frequencies and a second set of frequencies into the multi-phase fluid,
    wherein the sensing device comprises an enclosure containing an antenna and a dielectric layer that is placed in direct contact with the multi-phase fluid, the dielectric layer covering the antenna such that the antenna is located on a first side of the dielectric layer, and a second side of the dielectric layer, opposite the first side, is uncovered by the enclosure;
    wherein the uncovered side of the dielectric layer is placed in direct contact with the multi-phase fluid; and
    wherein the antenna and the dielectric layer are selected such that resonance is exhibited in at least one of the first set of frequencies and the second set of frequencies based on a flow state of the multi-phase fluid;
    receiving transmitted or reflected electromagnetic waves from the multi-phase fluid;
    selecting the flow state of the multi-phase fluid based on a classification parameter, wherein the classification parameter is determined from an analysis of the transmitted or reflected electromagnetic waves in at least one of the first set of frequencies and second set of frequencies; and
    determining the fraction of the one or more phases in the multi-phase fluid utilizing at least one fraction determination model, wherein the fraction determination model is selected based on the flow state of the multi-phase fluid.

2. The method of claim 1, further comprising determining one or more parameters from the transmitted or reflected electromagnetic waves,
    wherein determining the one or more parameters comprises determining at least one of one or more resonant frequencies of the transmitted or reflected electromagnetic waves, an amplitude of the transmitted or reflected electromagnetic waves at the one or more resonant frequencies, a phase angle of the transmitted or reflected electromagnetic waves at the one or more resonant frequencies, a group delay of the transmitted or reflected electromagnetic waves, and combinations thereof.

3. The method of claim 2, wherein determining the classification parameter comprises determining if the one or more resonant frequencies comprise at least one frequency from the first set of frequencies and at least one frequency from the second set of frequencies.

4. The method of claim 3, further comprising selecting oil-continuous flow state as the multi-phase fluid flow state when the one or more resonant frequencies comprise frequencies from the first set of frequencies as well as the second set of frequencies.

5. The method of claim 3, further comprising selecting water-continuous flow state as the multi-phase fluid flow state when the one or more resonant frequencies comprise frequencies from the first set of frequencies.

6. The method of claim 2, further comprising determining a permittivity of the multi-phase fluid based on the one or more parameters.

7. The method of claim 6, further comprising utilizing the permittivity of the multiphase fluid and the fraction determination model to determine the fraction of the one or more phases of the multi-phase fluid.

8. The method of claim 1, wherein the antenna comprises a patch antenna.

9. The method of claim 1, further comprising placing the sensing device such that the dielectric layer conforms to an inner surface of the conduit.

10. A system for determining a fraction of one or more phases of a multi-phase fluid flowing in a conduit, the system comprising:
one or more sensing devices configured for placement placed on or about a conduit, wherein each sensing device comprises:
an enclosure;
an antenna positioned within the enclosure and configured to emit electromagnetic waves of a range of frequencies, wherein the at least one antenna is selected such resonance is exhibited in a first set of frequencies from the range of frequencies based on a flow state of the multi-phase fluid; and
a dielectric layer positioned within the enclosure and covering the antenna such that the antenna is positioned on a first side of the dielectric layer and a second side of the dielectric layer, opposite the first side is in direct contact with the multi-phase fluid and is uncovered by the enclosure,
wherein the antenna and the dielectric layer are selected such that resonance is exhibited in at least one of the first set of frequencies and a second set of frequencies based on the flow state of the multi-phase fluid; and
a controller configured to
excite the antenna at one or more frequencies from the range of frequencies, wherein the one or more frequencies comprise the first set of frequencies and the second set of frequencies,
acquire transmitted or reflected electromagnetic waves from the multi-phase fluid,
select the flow state of the multi-phase fluid based on a classification parameter,
wherein the classification parameter is determined from an analysis of the transmitted or reflected electromagnetic waves in at least one of the first set of frequencies and second set of frequencies, and
estimate the fraction of the one or more phases of the multi-phase fluid using a
fraction determination model and one or more parameters determined from the transmitted or reflected electromagnetic waves, wherein the fraction determination model is selected based on the selected flow state.

11. The system of claim 10, wherein the controller is configured to determine the one or more parameters based on the analysis of the transmitted or reflected electromagnetic waves.

12. The system of claim 11, wherein the controller is configured to determine a permittivity of the multi-phase fluid based on the one or more parameters of the transmitted or reflected electromagnetic waves.

13. The system of claim 12, wherein the controller is configured to determine the fractions of the one or more phases of the multi-phase fluid based on the permittivity of the multi-phase fluid and the fraction determination model.

14. The system of claim 10, further comprises a metallic enclosure configured to be placed along an outer surface of the antenna and the dielectric layer.

15. The system of claim 10, wherein the antenna comprises at least one of a patch antenna, a monopole antenna, a dipole antenna, an antenna feed, and a multi pole antenna.

16. The system of claim 10, wherein the side of the dielectric layer that is in direct contact with the multi-phase fluid is configured to conform to a shape of an inner surface of the conduit.

17. The system of claim 10, wherein the controller is further configured to:
detect if resonance is observed in the transmitted or reflected electromagnetic waves in the first set of frequencies as well as the second set of frequencies;
select oil-continuous as the flow state of the multi-phase fluid when resonance is observed in the first set of frequencies as well as the second set of frequencies; and
select water-continuous as the flow state of the multi-phase fluid when resonance is observed in the first set of frequencies alone.

18. The system of claim 10, wherein the first set of frequencies and the second set of frequencies are different.

19. A method for determining phase fractions in a multi-phase fluid that comprises a lossy phase, wherein the method comprises:
exciting a sensing device to cause the sensing device to emit electromagnetic waves of a range of frequencies into the multi-phase fluid,
wherein the sensing device comprises an enclosure containing an antenna and a dielectric layer that is placed in direct contact with the multi-phase fluid, the dielectric layer covering the antenna such that the antenna is located on a first side of the dielectric layer, (insert a comma) and a second side of the dielectric layer, opposite the first side, (insert a comma) is uncovered by the enclosure;
wherein the uncovered side of the dielectric layer is placed in direct contact with the multi-phase fluid; and
wherein resonance is exhibited at different frequencies based on a fraction of the lossy phase in the multi-phase fluid;
receiving transmitted or reflected electromagnetic waves from the multi-phase fluid; and
determining the fraction of the one or more phases in the multi-phase fluid utilizing at least one fraction determination model, wherein the fraction determination model comprises a relationship between the phase fractions and one or more parameters determined from the transmitted or reflected electromagnetic waves.

20. The method of claim 19, further comprises determining the one or more parameters based on an analysis of the transmitted or reflected electromagnetic waves.

* * * * *